United States Patent [19]

Theodoridis

[11] Patent Number: 4,878,941
[45] Date of Patent: Nov. 7, 1989

[54] HERBICIDES

[75] Inventor: George Theodoridis, Princeton, N.J.

[73] Assignee: FMC Corporation, Philadelphia, Pa.

[21] Appl. No.: 139,404

[22] Filed: Dec. 29, 1987

[51] Int. Cl.[4] .................. A01N 43/207; C07D 403/04
[52] U.S. Cl. ........................................ 71/93; 544/182
[58] Field of Search ............................ 544/182; 71/93

[56]  References Cited
U.S. PATENT DOCUMENTS 4,616,017 10/1986 Teraji et al. .................... 544/182
4,640,917 2/1987 Rosner et al. .................. 544/182

*Primary Examiner*—John M. Ford
*Attorney, Agent, or Firm*—Robert Kennedy; H. Robinson Ertelt; Abner Sheffer

[57]  ABSTRACT

Quinolinone compounds of the formula

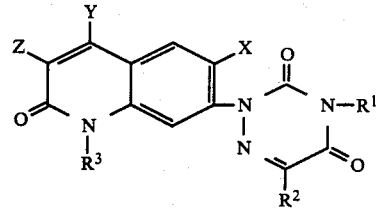

or

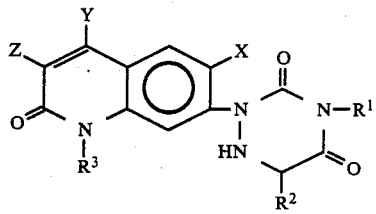

in which $R^3$ is H, alkyl, alkenyl, alkynyl, haloalkyl, haloalkenyl, alkoxyalkyl, alkoxyalkoxyalkyl, cycloalkyl, alkylthioalkyl, aralkyl, cyanoalkyl, alkoxycarbonylalkyl, hydroxy, or alkoxy; X is H, halogen, alkyl or haloalkyl; Y is H, halogen, alkyl, haloalkyl, alkoxycarbonyl, cyano, or nitro; Z is H, halogen, alkyl, haloalkyl, alkoxy, alkenyl, alkynyl, haloalkoxy, alkylthio, alkylsulfinyl, alkylsulfonyl, alkoxycarbonyl, cyano, or nitro; $R^1$ alkyl, alkenyl, alkynyl, haloalkyl alkoxyalkyl, or haloalkoxyalkyl; and $R^2$ is H, alkyl, haloalkyl, alkoxy, haloalkoxy, alkylthio, alkylsulfinyl, alkyl, alkoxy, halolkoxy, alkylthio, alkylsulfinyl, alkylsulfonyl, or halogen; and the corresponding 3,4-dihydroquinolinone compounds as herbicides.

49 Claims, No Drawings

HERBICIDES

The invention described in this application pertains to weed control in agriculture, horticulture, and other fields where there is a desire to control unwanted plant growth. More specifically, the present application describes certain herbicidal aryl triazinediones, compositions of them, methods of preparing them, and methods for preventing or destroying undesired plant growth by preemergence or postemergence application of the herbicidal compositions to the locus where control is desired. The present compounds may be used to effectively control a variety of both grassy and broadleaf plant species.

One aspect of this invention relates to triazinediones of the following formula I and their use as herbicides:

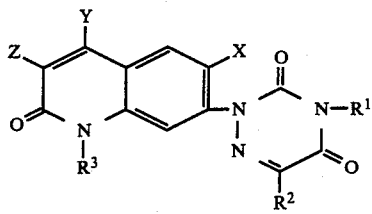

Formula I in which $R^3$ is:
H;
alkyl, e.g. methyl, ethyl, propyl, or isopropyl;
alkenyl, e.g. allyl or methallyl;
alkynyl, e.g. propynyl or methylpropynyl;
haloalkyl, e.g. 3-chloropropyl, 2-fluoroethyl, or 3-fluoropropyl;
haloalkenyl, e.g. 3,3-dichloro-2-propenyl;
alkoxyalkyl, e.g. methoxymethyl or ethoxymethyl;
alkoxyalkoxyalkyl, e.g. ethoxymethoxymethyl;
cycloalkyl, e.g. cyclopropylmethyl;
alkylthioalkyl, e.g. methylthiomethyl;
aralkyl, e.g. benzyl;
cyanoalkyl, e.g. cyanomethyl;
alkoxycarbonylalkyl e.g. methoxycarbonylmethyl; hydroxy;
or alkoxy, e.g. methoxy or ethoxy.
X is H, halogen (such as F, Cl or Br), alkyl (e.g. methyl), or haloalkyl (e.g. difluoromethyl);
Y is H, halogen (e.g. F, Cl or Br), alkyl (e.g. methyl), haloalkyl (e.g. difluoromethyl), alkoxycarbonyl (e.g. ethoxycarbonyl), cyano, or nitro.
Z is H, halogen (e.g. F, Cl or Br), alkyl (e.g. methyl), haloalkyl (e.g. difluoromethyl), alkoxy (e.g. methoxy), alkenyl (e.g. allyl), alkynyl (e.g. propynyl), haloalkoxy (e.g. difluoromethoxy), alkylthio (e.g. methylthio), alkylsulfinyl (e.g. methylsulfinyl), alkylsulfonyl (e.g. methylsulfonyl), alkoxycarbonyl (e.g. ethoxycarbonyl), cyano, or nitro.
$R^1$ is alkyl (e.g. methyl), alkenyl (e.g. allyl), alkynykl (e.g. propynyl), haloalkyl (e.g. difluoromethyl, 2-fluoroethyl, or 3-fluoropropyl), alkoxyalkyl (e.g. methoxymethyl), or haloalkoxyalkyl (e.g. difluoromethoxymethyl).
$R^2$ is H, alkyl (e.g. methyl), haloalkyl (e.g. difluoromethyl), alkoxy, (e.g. methoxy), haloalkoxy (e.g. difluoromethoxy), alkylthio (e.g. methylthio), alkylsulfinyl (e.g. methylsulfinyl), alkylsulfonyl (e.g. methylsulfonyl), or halogen (e.g. F, Cl, or Br).

In each aspect of the invention it is often preferable that any alkyl, alkenyl, alkynyl or alkylene group or moiety (such as the hydrocarbon moiety of an alkoxy or haloalkoxy group) have up to 6 carbon atoms, e.g 1 to 4 carbon atoms and any cycloalkyl have 3 to 7 ring carbon atoms.

The compounds of this invention may be prepared by the use of steps generally described in the literature or in the following Example or by methods analogous or similar thereto and within the skill of the art. In the Example below, a compound of the formula

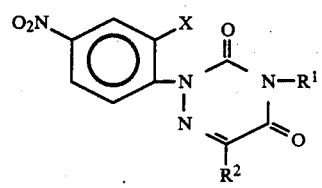

Formula II is reduced to convert the nitro group to an amino group, after which the resulting amino compound is reacted with a compound of the formula YHC=C(-Z)—C(O)—$X^3$ where $X^3$ is, for instance, a lower alkoxy group. This reaction is effected, according to a modification of the known Meerwein reaction involving formation of a diazonium halide and its reaction with an olefin in the presence of a copper halide, to form a compound of the formula

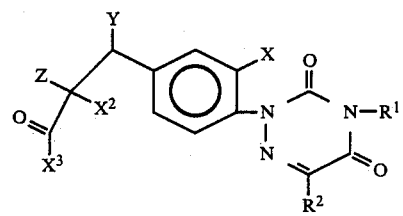

Formula III where $X^2$ is halogen (such as Cl or Br). The resulting compound is then nitrated to form a compound of the formula

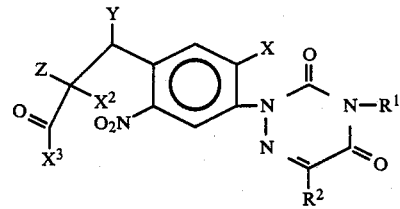

Formula IV

Then, by reaction involving treatment with iron in an acidified solvent, (e.g. at an elevated temperature such as 40°-150° C.), the nitro group is reduced and ring closure is effected, forming a dihydroquinolinone of the formula

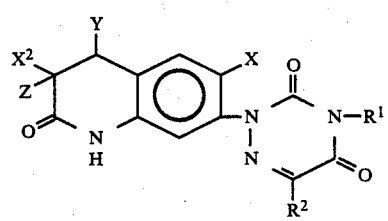

Formula V

The dihydroquinolinone is then dehydrohalogenated, as by treatment with a base such as triethylamine, to form a quinolinone of the formula

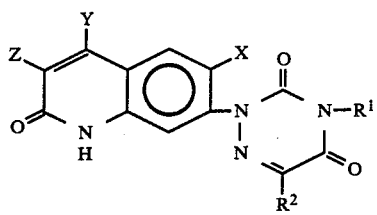

Formula VI $R^3$ groups other than hydrogen may then be introduced by reaction with $R^3X^4$ wherein $X^4$ is a leaving group such as halogen, e.g. Br or I.

As indicated above, the process involves the use of a reactant of the formula YHC=C(Z)—C(O)—$X^3$. Among the reactants of this type which may be used are the following: methyl acrylate, ethyl acrylate, methyl methacrylate, methyl crotonate, methyl 3-chloroacrylate, methyl 2-methylene-4-pentenoate, and methyl 2-methylene-4-pentynoate.

To produce compounds in which $R^3$ is hydroxy or alkoxy the reduction and ring closure step may be effected by using a milder reducing agent (such as hydrazine in the presence of rhodium on carbon) to form, during the reaction, an intermediate having an —NHOH group (instead of an —NH$_2$ group) at the 5-position of the benzene ring so that on cyclization and dehydrohalogenation there is formed a compound having the formula

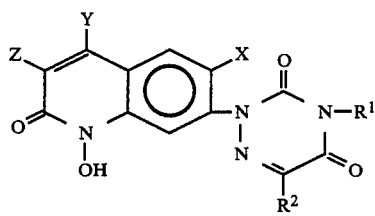

Formula VII after which that compound may be treated with an appropriate alkylating agent in the presence of a base (e.g. methyl iodide in the presence of NaH).

Under some reaction conditions the above-mentioned reaction with iron may also result in the formation of a herbicidal by-product which is a dihydroquinolinone of the formula

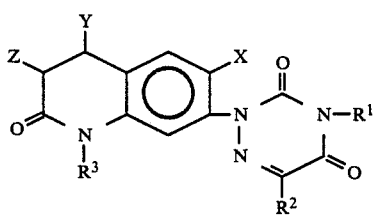

Formula VIII

Dihydroquinolinones of formula VIII may also be produced by a catalytic hydrogenation (e.g. under basic conditions) of the above-illustrated quinolinones (e.g. of formula I or VI) and are also useful as herbicides.

Dihydrotriazinediones are also within the scope of the invention and may be prepared by hydrogenation of the triazene ring at an early stage of the process. For instance the reduction of a compound of formula II may be effected so as to not only reduce the NO$_2$ group but also hydrogenate the triazine ring, producing a dihydrotriazinedione compound of the following formula

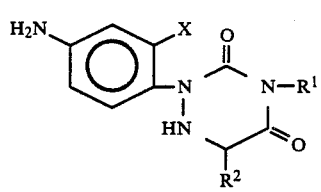

Formula IX

This compound may be subjected to the same steps as described above, thereby producing intermediates like those of formulas III, IV, V and VI except that the triazine ring is hydrogenated, and eventually yielding a herbicidal compound of the following formula

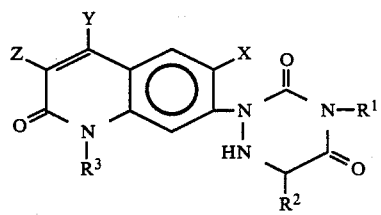

Formula X

The corresponding dihydroquinolinones are also herbicidal and are within the scope of the invention.

Representative compounds of this invention are tabulated below in Table 1. The following Example is given to illustrate this invention further.

EXAMPLE

1-[6-FLUORO-1-[2-PROPYNYL]QUINOLIN-2(1H)-ONE-7-YL]-4-METHYL-1,2,4-TRIAZINE-3,5(2H,4H)-DIONE

From the reaction of 3,4-difluoronitrobenzene with hydrazine in isopropyl alcohol at an elevated temperature (e.g. 75°–85° C.) there is produced 2-fluoro-4-nitrophenylhydrazine. The latter is then treated with acetone and sulfuric acid in tetrahydrofuran to yield N'-(2-fluoro-4-nitrophenyl)-dimethylketone hydrazone. The latter is then treated with potassium cyanate in aqueous acetic acid to produce 1-(2-fluoro-4-nitrophenyl)-5,5-dimethyl-1,2,4-triazolidin-3-one. The latter is then reacted with pyruvic acid and sulfuric acid in 1,4-dioxane to form 2-(2-fluoro-4-nitrophenyl-1,2,4-triazine-3,4(2H,4H)-dione. The latter is then reacted first with sodium hydride in dimethylformamide followed by methyl iodide to yield 2-(2-fluoro-4-nitrophenyl)-4-methyl-1,2,4-triazine-3,5(2H,4H)-dione. The latter is treated with iron powder in acetic acid to yield 2-(4-amino-2-fluorophenyl)-4-methyl-1,2,4-triazine-3,5(2H,4H)-dione. The latter dione is treated first with sodium nitrite in acetone and hydrochloric acid, then with methyl acrylate, and lastly with copper (I) chloride to form methyl 2-chloro-3-[5-fluoro-4-[4-methyl-1,2,4-triazine-3,5(2H,4H)-dione-1-yl]phenyl]propionate. The latter is then nitrated by treatment with a mixture of nitric acid and sulfuric acid to form methyl 2-chloro-3-[5-fluoro-4-[4-methyl-1,2,4-triazine-3,5(2H,4H)-dione-1-yl]-2-nitrophenyl]propionate. The latter is dissolved in acetic acid and added to a hot suspension of iron powder in acetic acid, then heated at an elevated temperature (e.g. 80°–90° C.) for about one hour to form 1-(3-chloro-6-fluoro-3,4-dihydroquinolin-2(1H)-one-7-yl)-4-methyl-1,2,4-triazine-3,5,(2H,4H)-dione. The latter is dehydrohalogenated with triethylamine in tetrahydrofuran to yield 1-[6-fluoroquinolin-2(1H)-one-7-yl]-4-methyl-1,2,4-triazine-3,5(2H,4H)-dione. The latter is dissolved in dimethylformamide and treated first with potassium carbonate followed by propargyl chloride to yield 1-[6-fluoro-1-[2-propynyl]quinolin-2(1H)-one-7-yl]-4-methyl-1,2,4-triazine-3,5(2H,4H)-dione.

For herbicidal application, the active compounds are formulated into herbicidal compositions by admixture in herbicidally effective amounts with adjuvants and carriers normally employed in the art for facilitating the dispersion of active ingredients for the particular utility desired, recognizing the fact that the formulation and mode of application of a toxicant may effect the activity of the material in a given application. Thus, for agricultural use the present herbicidal compounds may be formulated as granules of relatively large particle size, as water-soluble or water-dispersible granules, as powdery dusts, as wettable powders, as emulsifiable concentrates, as solutions, or as any of several other known types of formulations, depending on the desired mode of application.

These herbicidal compositions may be applied either as water-diluted sprays, or dusts, or granules to the areas in which suppression of vegetation is desired. These formulations may contain as little as 0.1%, 0.2% or 0.5% to as much as 95% or more by weight of active ingredient.

Dusts are free flowing admixtures of the active ingredient with finely divided solids such as talc, natural clays, kieselguhr, flours such as walnut shell and cottonseed flours, and other organic and inorganic solids which act as dispersants and carriers for the toxicant; these finely divided solids have an average particle size of less than about 50 microns. A typical dust formulation useful herein is one containing 1.0 part or less of the herbicidal compound and 99.0 parts of talc.

Wettable powders, also useful formulations for both pre- and postemergence herbicides, are in the form of finely divided particles which disperse readily in water or other dispersant. The wettable powder is ultimately applied to the soil either as a dry dust or as an emulsion in water or other liquid. Typical carriers for wettable powders include Fuller's earth, kaolin clays, silicas, and other highly absorbent, readily wet inorganic diluents. Wettable powders normally are prepared to contain about 5–80% of active ingredient, depending on the absorbency of the carrier, and usually also contain a small amount of a wetting, dispersing or emulsifying agent to facilitate dispersion. For example, a useful wettable powder formulation contains 80.8 parts of the herbicidal compound 17.9 parts of Palmetto clay, and 1.0 part of sodium lignosulfonate and 0.3 part of sulfonated aliphatic polyester as wetting agents. Other wettable powder formulations are:

| Component: | % by Wt. |
|---|---|
| Active ingredient | 40.00 |
| Sodium lignosulfonate | 20.00 |
| Attapulgite clay | 40.00 |
| Total | 100.00 |
| Active ingredient | 90.00 |
| Dioctyl sodium sulfosuccinate | 0.10 |
| Synthetic fine silica | 9.90 |
| Total | 100.00 |
| Active ingredient | 20.00 |
| Sodium alkylnaphthalenesulfonate | 4.00 |
| Sodium lignosulfonate | 4.00 |
| Low viscosity methyl cellulose | 3.00 |
| Attapulgite clay | 69.00 |
| Total | 100.00 |
| Active ingredient | 25.00 |
| Base: | 75.00 |
| 96% hydrated aluminum magnesium silicate | |
| 2% powdered sodium lignosulfonate | |
| 2% powdered anionic sodium alkyl-naphthalenesulfonate | |
| Total | 100.00 |

Frequently, additional wetting agent and/or oil will be added to the tank-mix for postemergence application to facilitate dispersion on the foliage and absorption by the plant.

Other useful formulations for herbicidal applications are emulsifiable concentrates (ECs) which are homogeneous liquid or paste compositions dispersible in water or other dispersant, and may consist entirely of the herbicidal compound and a liquid or solid emulsifying agent, or may also contain a liquid carrier, such as xylene, heavy aromatic naphthas, isophorone, or other non-volatile organic solvent. For herbicidal application these concentrates are dispersed in water or other liquid carrier, and normally applied as a spray to the area to be treated. The percentage by weight of the essential active ingredient may vary according to the manner in which the composition is to be applied, but in general comprises 0.5 to 95% of active ingredient by weight of the herbicidal composition.

The following are specific examples of emulsifiable concentrate formulations:

| Component: | % by Wt. |
|---|---|
| Active ingredient | 53.01 |
| Blend of alkylnaphthalenesulfonate and polyoxyethylene ethers | 6.00 |
| Epoxidized soybean oil | 1.00 |
| Xylene | 39.99 |
| Total | 100.00 |
| Active ingredient | 10.00 |
| Blend of alkylnaphthalenesulfonate and polyoxyethylene ethers | 4.00 |
| Xylene | 86.00 |
| Total | 100.00 |

Flowable formulations are similar to ECs except that the active ingredient is suspended in a liquid carrier, generally water. Flowables, like ECs, may include a small amount of a surfactant, and contain active ingredient in the range of 0.5 to 95%, frequently from 10 to 50%, by weight of the composition. For application, flowables may be diluted in water or other liquid vehicle, and are normally applied as a spray to the area to be treated.

The following are specific examples of flowable formulations:

| Component: | % by Wt. |
|---|---|
| Active ingredient | 46.00 |
| Colloidal magnesium aluminum silicate | 0.40 |
| Sodium alkylnaphthalenesulfonate | 2.00 |
| Paraformaldehyde | 0.10 |
| Water | 40.70 |

| Component: | | % by Wt. |
| --- | --- | --- |
| Propylene glycol | | 7.50 |
| Acetylenic alcohols | | 2.50 |
| Xanthan gum | | 0.80 |
| | Total | 100.00 |
| Active ingredient | | 45.00 |
| Water | | 48.50 |
| Purified smectite clay | | 2.00 |
| Xanthan gum | | 0.50 |
| Sodium alkylnaphthalenesulfonate | | 1.00 |
| Acetylenic alcohols | | 3.00 |
| | Total | 100.00 |

Typical wetting, dispersing or emulsiying agents used in agricultural formulations include, but are not limited to, the alkyl and alkylaryl sulfonates and sulfates and their sodium salts; alkylaryl polyether alcohols; sulfated higher alcohols; polyethylene oxides; sulfonated animal and vegetable oils; sulfonated petroleum oils; fatty acid esters of polyhydric alcohols and the ethylene oxide addition products of such esters; and the addition product of long-chain mercaptans and ethylene oxide. Many other types of useful surface-active agents are available in commerce. The surface-active agent, when used, normally comprises from 1 to 15% by weight of the composition.

Other useful formulations include simple solutions or suspensions of the active ingredient in a relatively non-volatile solvent such as water, corn oil, kerosene, propylene glycol, or other suitable solvents. The following illustrate specific suspensions:

| Oil Suspension: | | % by Wt. |
| --- | --- | --- |
| Active ingredient | | 25.00 |
| polyoxyethylene sorbitol hexaoleate | | 5.00 |
| Highly aliphatic hydrocarbon oil | | 70.00 |
| | Total | 100.00 |
| Aqueous Suspension: | | |
| Active ingredient | | 40.00 |
| Polyacrylic acid thickener | | 0.30 |
| Dodecylphenol polyethylene glycol ether | | 0.50 |
| Disodium phosphate | | 1.00 |
| Monosodium phosphate | | 0.50 |
| Polyvinyl alcohol | | 1.00 |
| Water | | 56.70 |
| | Total | 100.00 |

Other useful formulations for herbicidal applications include simple solutions of the active ingredient in a solvent in which it is completely soluble at the desired concentration, such as acetone, alkylated naphthalenes, xylene, or other organic solvents. Granular formulations, wherein the toxicant is carried on relatively coarse particles, are of particular utility for aerial distribution or for penetration of cover crop canopy. Pressurized sprays, typically aerosols wherein the active ingredient is dispersed in finely divided form as a result of vaporization of a low boiling dispersant solvent carrier, such as the Freon fluorinated hydrocarbons, may also be used. Water-soluble water-dispersible granules are also useful formulations for herbicidal application of the present compounds. Such granular formulations are free-flowing, non-dusty, and readily water-soluble or water-miscible. The soluble or dispersible granular formulations described in U.S. Pat. No. 3,920,442 are useful herein with the present herbicidal compounds. In use by the farmer on the field, the granular formulations, emulsifiable concentrates, flowable concentrates, solutions, etc., may be diluted with water to give a concentration of active ingredient in the range of say 0.1% or 0.2% to 1.5% or 2%.

The active herbicidal compounds of this invention may be formulated and/or applied with insecticides, fungicides, nematicides, plant growth regulators, fertilizers, or other agricultural chemicals and may be used as effective soil sterilants as well as selective herbicides in agriculture. In applying an active compound of this invention, whether formulated alone or with other agricultural chemicals, an effective amount and concentration of the active compound is of course employed. Weed control may be achieved at low herbicide concentrations, such as 0.03 kg/ha.

The active herbicidal compounds of this invention may be used in combination with other herbicides, e.g. they may be mixed with, say, an equal or larger amount of a known herbicide such as chloroacetanilide herbicides such as 2-chloro-N-(2,6-diethylphenyl)-N-(methoxymethyl)acetamide (alachlor), 2-chloro-N-(2-ethyl-6-methylphenyl-N-(2-methoxy-1-methylethyl)acetamide (metolachlor), and N-chloroacetyl-N-(2,6-diethylphenyl)glycine (diethatyl-ethyl); benzothiadiazinone herbicides such as 3-(1-methylethyl)-(1H)-2,1,3-benzothiadiazin-4-(3H)-one-2,2-dioxide (bentazon); triazine herbicides such as 6-chloro-N-ethyl-N-(1-methylethyl)-1,3,5-triazine-2,4-diamine (atrazine), and 2-[4-chloro-6-(ethylamino)-1,3,5-triazin-2-yl]amino-2-methylpropanenitrile (cyanazine); dinitroaniline herbicides such as 2,6-dinitro-N,N-dipropyl-4-(trifluoromethyl)-benzeneamine (trifluralin); aryl urea herbicides such as N'-(3,4-dichlorophenyl)-N,N-dimethylurea (diuron) and N,N-dimethyl-N'-[3-(trifluoromethyl)phenyl]urea (fluometuron); and 2-[(2-chlorophenyl)methyl]-4,4-dimethyl-3-isoxazolidinone.

It is apparent that various modifications may be made in the formulation and application of the compounds of this invention without departing from the inventive concepts herein as defined in the claims.

TABLE 1

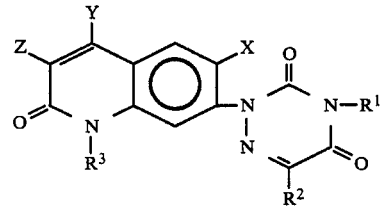

| Cmpd No. | R¹ | R² | R³ | X | Y | Z |
| --- | --- | --- | --- | --- | --- | --- |
| 1 | CH₃ | H | CH₃ | F | H | H |
| 2 | CH₃ | H | C₂H₅ | F | H | H |

TABLE 1-continued

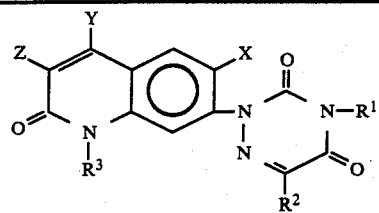

| Cmpd No. | R¹ | R² | R³ | X | Y | Z |
|---|---|---|---|---|---|---|
| 3 | CH₃ | H | n-C₃H₇ | Cl | H | H |
| 4 | CH₃ | H | n-C₃H₇ | Br | H | H |
| 5 | CH₃ | H | n-C₃H₇ | F | H | H |
| 6 | CH₃ | H | n-C₃H₇ | F | H | Cl |
| 7 | CH₃ | H | n-C₃H₇ | F | H | Br |
| 8 | CH₃ | H | n-C₃H₇ | F | H | F |
| 9 | CH₃ | H | n-C₃H₇ | F | H | CH₃ |
| 10 | CH₃ | H | n-C₃H₇ | F | H | CH(CH₃)₂ |
| 11 | CH₃ | H | n-C₃H₇ | F | H | CHF₂ |
| 12 | CH₃ | H | n-C₃H₇ | F | H | CF₃ |
| 13 | CH₃ | H | n-C₃H₇ | F | H | OCH₃ |
| 14 | CH₃ | H | n-C₃H₇ | F | H | OCHF₂ |
| 15 | CH₃ | H | n-C₃H₇ | F | H | SCH₃ |
| 16 | CH₃ | H | n-C₃H₇ | F | H | SO₂CH₃ |
| 17 | CH₃ | H | n-C₃H₇ | F | H | NO₂ |
| 18 | CH₃ | H | n-C₃H₇ | F | Cl | H |
| 19 | CH₃ | H | n-C₃H₇ | F | Br | H |
| 20 | CH₃ | H | n-C₃H₇ | F | CH₃ | H |
| 21 | CH₃ | H | n-C₃H₇ | F | CHF₂ | H |
| 22 | CH₃ | H | n-C₃H₇ | F | NO₂ | H |
| 23 | CH₃ | H | n-C₃H₇ | CH₃ | H | H |
| 24 | CH₃ | H | n-C₃H₇ | C₂H₅ | H | H |
| 25 | CH₃ | H | n-C₃H₇ | CHF₂ | H | H |
| 26 | CH₃ | H | n-C₃H₇ | CF₃ | H | H |
| 27 | CH₃ | H | CH(CH₃)₂ | F | H | H |
| 28 | CH₃ | H | n-C₄H₉ | F | H | H |
| 29 | CH₃ | H | CH₂CH₂CH(CH₃)₂ | F | H | H |
| 30 | CH₃ | H | CH₂CH₂F | F | H | H |
| 31 | CH₃ | H | CH₂CH₂CH₂F | F | H | H |
| 32 | CH₃ | H | CHF₂ | F | H | H |
| 33 | CH₃ | H | OCH₃ | F | H | H |
| 34 | CH₃ | H | CH₂OCH₃ | F | H | H |
| 35 | CH₃ | H | CH₂CH₂OCH₃ | F | H | H |
| 36 | CH₃ | H | CH₂CN | F | H | H |
| 37 | CH₃ | H | CH₂CH=CH₂ | F | H | H |
| 38 | CH₃ | H | CH₂CCl=CH₂ | F | H | H |
| 39 | CH₃ | H | CH₂C≡CH | F | H | H |
| 40 | CH₃ | H | CH₂CO₂CH₃ | F | H | H |
| 41 | CH₃ | C₂H₅ | n-C₃H₇ | F | H | H |
| 42 | CH₃ | n-C₃H₇ | n-C₃H₇ | F | H | H |
| 43 | CH₃ | Cl | n-C₃H₇ | F | H | H |
| 44 | CH₃ | Br | n-C₃H₇ | F | H | H |
| 45 | CH₃ | F | n-C₃H₇ | F | H | H |
| 46 | CH₃ | CH(CH₃)₂ | n-C₃H₇ | F | H | H |
| 47 | CH₃ | C(CH₃)₃ | n-C₃H₇ | F | H | H |
| 48 | CH₃ | CF₃ | n-C₃H₇ | F | H | H |
| 49 | CH₃ | OCH₃ | n-C₃H₇ | F | H | H |
| 50 | CH₃ | OCHF₂ | n-C₃H₇ | F | H | H |
| 51 | CH₃ | SCH₃ | n-C₃H₇ | F | H | H |
| 52 | C₂H₅ | H | n-C₃H₇ | F | H | H |
| 53 | n-C₃H₇ | H | n-C₃H₇ | F | H | H |
| 54 | CH(CH₃)₂ | H | n-C₃H₇ | F | H | H |
| 55 | CH₂CH₂F | H | n-C₃H₇ | F | H | H |
| 56 | CH₂OCH₃ | H | n-C₃H₇ | F | H | H |
| 57 | CH₂CH=CH₂ | H | n-C₃H₇ | F | H | H |
| 58 | CH₂C≡CH | H | n-C₃H₇ | F | H | H |
| 59 | CH₃ | H | H | F | H | H |
| 60 | CH₃ | H | CH₂OCH₂OC₂H₅ | F | H | H |
| 61 | CH₃ | H | CH₂CHCH₂CH₂ | F | H | H |
| 62 | CH₃ | H | CH(CH₂)₄CH₂ | F | H | H |
| 63 | CH₃ | H | CH₂SCH₃ | F | H | H |
| 64 | CH₃ | H | CH₂C₆H₅ | F | H | H |
| 65 | CH₃ | H | OH | F | H | H |

TABLE 1-continued

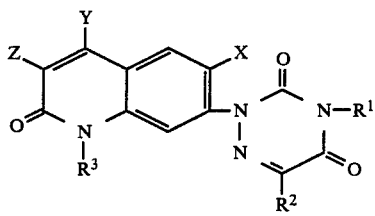

| Cmpd No. | R¹ | R² | R³ | X | Y | Z |
|---|---|---|---|---|---|---|
| 66 | CH₃ | H | n-C₃H₇ | H | H | H |
| 67 | CH₃ | H | n-C₃H₇ | F | F | H |
| 68 | CH₃ | H | n-C₃H₇ | F | CO₂C₂H₅ | H |
| 69 | CH₃ | H | n-C₃H₇ | F | CN | H |
| 70 | CH₃ | H | n-C₃H₇ | F | H | CH₂CH=CH₂ |
| 71 | CH₃ | H | n-C₃H₇ | F | H | CH₂C≡CH |
| 72 | CH₃ | H | n-C₃H₇ | F | H | S(O)CH₃ |
| 73 | CH₃ | H | n-C₃H₇ | F | H | CO₂C₂H₅ |
| 74 | CH₃ | H | n-C₃H₇ | F | H | CN |
| 75 | CH₂OCHF₂ | H | n-C₃H₇ | F | H | H |
| 76 | CH₃ | S(O)CH₃ | n-C₃H₇ | F | H | H |
| 77 | CH₃ | S(O)₂CH₃ | n-C₃H₇ | F | H | H |

I claim:
1. A herbicidal compound of the formula

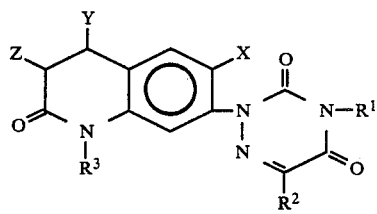

in which:
   $R^3$ is H, alkyl, alkenyl, alkynyl, haloalkyl, haloalkenyl, alkoxyalkyl, alkoxyalkoxyalkyl, cycloalkyl, alkylthioalkyl, benzyl, cyanoalkyl, alkoxycarbonylalkyl, hydroxy or alkoxy;
   X is H, halogen, alkyl, or haloalkyl;
   Y is H, halogen, alkyl, haloalkyl, alkoxycarbonyl, cyano, or nitro;
   Z is H, halogen, alkyl, haloalkyl, alkoxy, alkenyl, alkynyl, haloalkoxy, alkylthio, alkylsulfinyl, alkylsulfonyl, alkoxycarbonyl, cyano, or nitro;
   $R^1$ is alkyl, alkenyl, alkynyl, haloalkyl, alkoxyalkyl, or haloalkoxyalkyl; and
   $R^2$ is H, alkyl, haloalkyl, alkoxy, haloalkoxy, alkylthio, alkylsulfinyl, alkylsulfonyl, or halogen;
   and in which any alkyl, alkenyl, alkynyl or alkylene group or moiety has up to 6 carbon atoms and any cycloalkyl has 3 to 7 ring carbon atoms.

2. The herbicidal compound of claim 1 in which any alkyl, alkenyl, alkynyl or alkylene group or moiety has up to 4 carbon atoms.

3. The compound of claim 2 in which R² is H.

4. The compound of claim 3 in which R¹ is alkyl.

5. The compound of claim 4 in which X is halogen.

6. The compound of claim 5 in which Y is H.

7. The compound of claim 6 in which Z is H, halogen, or alkyl.

8. The compound of claim 7 in which R³ is alkyl, allyl, methallyl, propynyl, methylpropynyl, 3-chloropropyl, 2-fluoroethyl, 3-fluoropropyl, 3,3-dichloro-2-propenyl, methoxymethyl, ethoxymethyl, ethoxymethoxymethyl, cyclopropylmethyl, methylthiomethyl, benzyl, cyanomethyl, alkoxycarbonylmethyl, hydroxy, methoxy, or ethoxy.

9. The compound of claim 8 in which R³ is alkyl.

10. The compound of claim 9 in which X is F and Z is H.

11. The compound of claim 10 in which R¹ is CH₃.

12. The compound of claim 11 in which R³ is n-C₃H₇.

13. An herbicidal composition comprising an herbicidally effective amount of the compound of claim 1 in admixture with a suitable carrier.

14. A method for controlling undesired plant growth which comprises applying to the locus where control is desired an herbicidally effective amount of the composition of claim 13.

15. An herbicidal compound of the formula

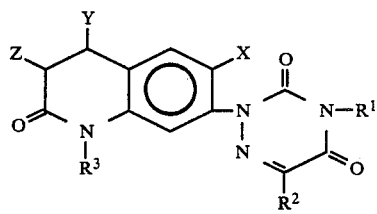

in which:
   $R^3$ is H, alkyl, alkenyl, alkynyl, haloalkyl, haloalkenyl, alkoxyalkyl, alkoxyalkoxyalkyl, cycloalkyl, alkylthioalkyl, benzyl, cyanoalkyl, alkoxycarbonylalkyl, hydroxy, or alkoxy;
   X is H, halogen, alkyl, or haloalkyl;
   Y is H, halogen, alkyl, haloalkyl, alkoxycarbonyl, cyano, or nitro;
   Z is H, halogen, alkyl, haloalkyl, alkoxy, alkenyl, alkynyl, haloalkoxy, alkylthio, alkylsulfinyl, alkylsulfonyl, alkoxycarbonyl, cyano, or nitro;
   $R^1$ is alkyl, alkenyl, alkynyl, haloalkyl, alkoxyalkyl, or haloalkoxyalkyl; and
   $R^2$ is H, alkyl, haloalkyl, alkoxy, haloalkoxy, alkylthio, alkylsulfinyl, alkylsulfonyl, or halogen;
   and in which any alkyl, alkenyl, alkynyl, or alkylene group or moiety has up to 6 carbon atoms and cycloalkyl has 3 to 7 carbon atoms.

16. The compound of claim 15 in which any alkyl, alkenyl, alkynyl, or alkylene group or moiety has up to 4 carbon atoms.

17. The compound of claim 16 in which $R^1$ is $CH_3$, $R^2$ is H, X is F, Y is H or halogen, Z is H, halogen, or alkyl, and $R^3$ is alkyl.

18. The compound of claim 17 in which Y is H, Z is H and $R^3$ is n-$C_3H_7$

19. An herbicidal composition comprising an herbicidally effective amount of the compound of claim 15 in admixture with a suitable carrier.

20. A method for controlling undesired plant growth which comprises applying to the locus where control is desired an herbicidally effective amount of the composition of claim 19.

21. An herbicidal composition comprising an herbicidally effective amount of the compound of claim 16 in admixture with a suitable carrier.

22. A method for controlling undesired plant growth which comprises applying to the locus where control is desired an herbicidally effective amount of the composition of claim 21.

23. A herbicidal compound of the formula

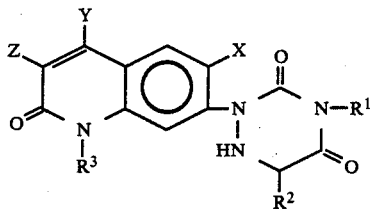

in which:
$R^3$ is H, alkyl, alkenyl, alkynyl, haloalkyl, haloalkenyl, alkoxyalkyl, alkoxyalkoxyalkyl, cycloalkyl, alkylthioalkyl, benzyl, cyanoalkyl, alkoxycarbonylalkyl, hydroxy, or alkoxy;

x is H, halogen, alkyl, or haloalkyl;

Y is H, halogen, alkyl, haloalkyl, alkoxycarbonyl, cyano, or nitro;

Z is H, halogen, alkyl, haloalkyl, alkoxy, alkenyl, alkynyl, haloalkoxy, alkylthio, alkylsulfinyl, alkylsulfonyl, alkoxycarbonyl, cyano, or nitro;

$R^1$ is alkyl, alkenyl, alkynyl, haloalkyl, alkoxyalkyl, or haloalkoxyalkyl; and $R^2$ is H, alkyl, haloalkyl, alkoxy, haloalkoxy, alkylthio, alkylsulfinyl, alkylsulfonyl, or halogen;

and in which any alkyl, alkenyl, alkynyl or alkylene group or moiety has up to 6 carbon atoms and any cycloalkyl has 3 to 7 ring carbon atoms.

24. The herbicidal compound of claim 23 in which any alkyl, alkenyl, alkynyl or alkylene group or moiety has up to 4 carbon atoms.

25. The compound of claim 24 in which $R^2$ is methyl.

26. The compound of claim 25 in which $R^1$ is haloalkyl.

27. The compound of claim 26 in which X is halogen.

28. The compound of claim 27 in which Y is H.

29. The compound of claim 28 in which Z is H or methyl.

30. The compound of claim 29 in which $R^3$ is alkyl, allyl, methallyl, propynyl, methylpropynyl, 3-chloropropyl, 2-fluoroethyl, 3-fluoropropyl, 3,3-dichloro-2-propenyl, methoxymethyl, ethoxymethyl, ethoxymethoxymethyl, cyclopropylmethyl, methylthiomethyl, benzyl, cyanomethyl, alkoxycarbonylmethyl, hydroxy, methoxy, or ethoxy.

31. The compound of claim 30 in which $R^3$ is alkyl.

32. The compound of claim 31 in which X is F and Z is H.

33. The compound of claim 32 in which $R^1$ is $CHF_2$.

34. The compound of claim 33 in which $R^3$ is n-$C_3H_7$.

35. An herbicidal composition comprising an herbicidally effective amount of the compound of claim 23 in admixture with a suitable carrier.

36. A method for controlling undesired plant growth which comprises applying to the locus where control is desired an herbicidally effective amount of the composition of claim 35.

37. An herbicidal compound of the formula

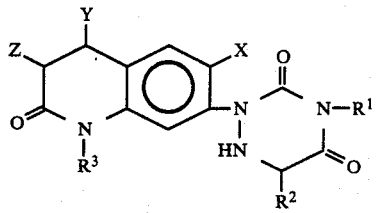

in which:
$R^3$ is H, alkyl, alkenyl, alkynyl, haloalkyl, haloalkenyl, alkoxyalkyl, alkoxyalkoxyalkyl, cycloalkyl, alkylthioalkyl, benzyl, cyanoalkyl, alkoxycarbonylalkyl, hydroxy, or alkoxy;

X is H, halogen, alkyl, or haloalkyl;

Y is H, halogen, alkyl, haloalkyl, alkoxycarbonyl, cyano, or nitro;

Z is H, halogen, alkyl, haloalkyl, alkoxy, alkenyl, alkynyl, haloalkoxy, alkylthio, alkylsulfinyl, alkysulfonyl, alkoxycarbonyl, cyano, or nitro;

$R^1$ is alkyl, alkenyl, alkynyl, haloalkyl, alkoxyalkyl, or haloalkoxyalkyl; and $R^2$ is H, alkyl, haloalkyl, alkoxy, haloalkoxy, alkylthio, alkylsulfinyl, alkylsulfonyl, or halogen; and in which any alkyl, alkenyl, alkynyl or alkylene group or moiety has up to 6 carbon atoms and cycloalkyl has 3 to 7 ring carbon atoms.

38. The herbicidal compound of claim 37 in which any alkyl, alkenyl, alkynyl or alkylene group or moiety has up to 4 carbon atoms.

39. The compound of claim 38 in which $R^2$ is methyl.

40. The compound of claim 39 in which $R^1$ is $CHF_2$.

41. The compound of claim 40 in which X is halogen.

42. The compound of claim 41 in which Y is H.

43. The compound of claim 42 in which Z is H.

44. The compound of claim 43 in which $R^3$ is alkyl, allyl, methallyl, propynyl, methylpropynyl, 3-chloropropyl, 2-fluoroethyl, 3-fluoropropyl, 3,3-dichloro-2-propenyl, methoxymethyl, ethoxymethyl, ethoxymethoxymethyl, cyclopropylmethyl, methylthiomethyl, benzyl, cyanomethyl, alkoxycarbonylmethyl, hydroxy, methoxy, or ethoxy.

45. The compound of claim 44 in which $R^3$ is alkyl.

46. The compound of claim 45 in which X is F.

47. The compound of claim 46 in which $R^3$ is n-$C_3H_7$.

48. An herbicidal composition comprising an herbicidally effective amount of the compound of claim 37 in admixture with a suitable carrier.

49. A method for controlling undesired plant growth which comprises applying to the locus where control is desired an herbicidally effective amount of the composition of claim 48.

* * * * *